(12) United States Patent
Ortega et al.

(10) Patent No.: US 6,332,890 B1
(45) Date of Patent: Dec. 25, 2001

(54) MICROKERATOTOME FOR THE DISSECTION OF LAMELLAE OF CORNEAL TISSUE

(75) Inventors: Angel Ramon Gutierrez Ortega; Emilio Sanz Amoros; Vicente Castello Pico, all of Valencia (ES)

(73) Assignee: Novosalud, S.L. (ES)

( * ) Notice: Subject to any disclaimer, the term of this patent is extended or adjusted under 35 U.S.C. 154(b) by 0 days.

(21) Appl. No.: 09/640,620

(22) Filed: Aug. 17, 2000

(51) Int. Cl.[7] .................................................... A61B 17/32
(52) U.S. Cl. .............................................................. 606/166
(58) Field of Search ................................... 606/166, 167, 606/169, 161, 107, 172

(56) References Cited

U.S. PATENT DOCUMENTS

| | | |
|---|---|---|
| 4,586,929 | 5/1986 | Binder . |
| 4,796,623 | 1/1989 | Krasner et al. . |
| 4,840,175 | 6/1989 | Peyman . |
| 5,496,339 | 3/1996 | Koepnick . |
| 5,560,657 | 10/1996 | Morgan . |
| 5,586,980 | 12/1996 | Kremer et al. . |
| 5,591,174 | 1/1997 | Clark et al. . |
| 5,779,723 | 7/1998 | Schwind . |
| 5,980,543 * | 11/1999 | Carriazo et al. ............... 606/166 |
| 5,989,272 | 11/1999 | Barron et al. . |
| 5,997,559 | 12/1999 | Ziemer . |
| 6,022,365 | 2/2000 | Aufaure et al. . |
| 6,071,293 * | 6/2000 | Krumeich ........................ 606/166 |
| 6,126,668 | 10/2000 | Bair et al. . |

FOREIGN PATENT DOCUMENTS

| | | |
|---|---|---|
| 0 442 156 B1 | 12/1993 | (EP) . |
| 0 771 553 A1 | 5/1997 | (EP) . |
| 0 873 735 A1 | 10/1998 | (EP) . |
| 0 895 764 A1 | 2/1999 | (EP) . |
| 0 956 841 A2 | 11/1999 | (EP) . |
| 0 971 659 A1 | 1/2000 | (EP) . |
| 1 027 873 A2 | 8/2000 | (EP) . |
| 2 150 863 | 12/2000 | (ES) . |
| WO 95/20920 | 8/1995 | (WO) . |
| WO 95/31143 | 11/1995 | (WO) . |
| WO 98/27901 | 7/1998 | (WO) . |
| WO 99/26568 | 6/1999 | (WO) . |
| WO 00/09055 | 2/2000 | (WO) . |
| WO 00/56222 | 9/2000 | (WO) . |
| WO 00/61015 | 10/2000 | (WO) . |

* cited by examiner

*Primary Examiner*—Kevin Truong
(74) *Attorney, Agent, or Firm*—Brinks Hofer Gilson & Lione

(57) ABSTRACT

A microkeratotome for the dissection of lamellae of corneal tissue includes a body (1) inside which a chassis (8) is housed where two motors (10) and (12) are installed which provide the oscillation of the corresponding cutting blade and the movement of the head (21) in which the cutting blade itself (20) is situated, all of which is combined with a suction ring (24) which immobilizes and imparts vacuum pressure to the eyeball through an orifice, the vacuum pressure being distributed simultaneously from the ring (24) through a peripheral channel situated in the same. The said ring is prevented from coming loose due to the maximum pressure reached in the eye when the unit is mounted upon it. It also includes an electronic control unit which has, according to the keratometry appropriate to the patient, several programmes which predefine cutting qualities.

11 Claims, 10 Drawing Sheets

MICROKERATOTOME FOR THE DISSECTION OF LAMELLAE OF CORNEAL TISSUE

BACKGROUND

The invention relates to a microkeratotome for the dissection of lamellae of corneal tissue, which has been conceived with characteristics that make it feasible to submerge it in sterilizing fluids for a practical and fast sterilization of the parts other than those of the mechanical transmission system which this type of apparatus includes, in order to reduce the time or interval between cornea-sectioning operations in which it is used, above all in cases where both eyes of the same patient are being operated on. The microkeratotome has means that make complete transparency possible in the cutting area, incorporating likewise an electronic unit with several cutting programmes to be selected according to the keratometry.

It is equally an object of the invention to provide a microkeratotome which gives optimal visibility to the surgeon during an operation, by virtue of the fact that the side pieces of the head have been made with a small height, and also the incorporation of a transparent plate in correspondence with the cutting area. Also, greater control during an operation is achieved by the microkeratotome of the invention due to the fact that the corresponding suction ring which immobilizes the eyeball has a specific size and design, being provided with a peripheral channel which uniformly and firmly distributes the vacuum pressure by means of which the eyeball is immobilized.

In 1949 Dr. José Barraquer, in Columbia, suggested that sight problems could be corrected by a surgical operation to change the curvature of the cornea. In its origins the procedure consisted of cutting a thin section from the frontal part of the cornea and subsequently freezing it to give the desired shape using a cryogenic lathe and then thawing it before implanting it.

The instrument used to make sections in the cornea is known as a Microkeratotome and the system upon which its action is based today is that of cutting a lamella of the desired thickness without complete detachment from the rest and forming a hinge which, when folded back, leaves an area of operation free for the laser, with which the curvature of the cornea will be modified by its action, and is subsequently refolded for cicatrization to take place.

In the last thirty years Microkeratotomes have been used with the aim of obtaining corneal lamellae of the desired size and thickness. An apparatus which immobilizes the eye has always been used, and another one which, in the manner of a "carpenter's plane", moves and cuts the lamella.

In the first models, the cutting apparatus was moved manually over the fixing ring.

There were, among others, three main problems:

1. The movement did not always follow the desired direction.
2. Manual movement did not provide a uniform speed of advance and this affects the thickness of the lamella obtained (the faster the advance, the less thickness obtained, and vice versa).
3. If the cutting part is raised above the plane of the eyeball immobilizer ring, the lamella is cut at that point, causing a serious complication.

Later, a rail was added to the fixing ring to act as a guide for the cutting part. In other variants two guides were introduced which prevented movements other than in the desired direction. In these models, the problems arising from manual movement with a non-uniform speed continued and the problem of undesired stoppages of the cutting part arose, due to blockages between the rails, which caused significant irregularities in the surface that was being cut.

Automatic movement of the cutting apparatus upon the ring appeared subsequently and with it the differences in thickness were eliminated, as the speed is uniform; some of these apparatus were even equipped with a programmable stop. The problems observed with the automatic model are:

Stoppages of the cutting part before it reaches the end of its path, caused by particles introduced between the two parts or between the gears of the cutting part, or due to mechanical or electrical failure of the system. This forces surgery to be suspended.

Oscillation speed of the blade insufficient for the speed with which the cutting part moves, which produces irregularities in the cutting surface and the edges.

Failure of the suction system due to faults in the pump (of the carbon blade type), or because the conjunctiva closes the hole through which vacuum pressure is applied to the eye.

An interchangeable front plate which makes it possible for the surgeon to forget to put it on, in which case the cutting thickness, being greater than that of the cornea, causes the eyeball to be pierced and serious damage to the internal structures.

Cutting diameter insufficient for some kinds of surgery.

Frequent failures in the movement system, situated in the motor, or in the transmission system due to its mechanical stopping system which causes the motor to overload and significant strain on the transmission. Water entering the transmission also causes it to deteriorate.

When the suction fails, the system does not detect it, and as it continues to cut it cuts the lamella with a shorter length, causing corneal scars.

Play in the movement system together with the fact that the dragging mechanism is produced on only one side tends to cause stoppages in the advance before reaching the end of the path.

While the advance is underway, the shape of the cutting part prevents the surgeon from seeing at what level it is taking place.

Other systems appeared which attempted to remedy some of the problems described, but they provided a cut of poor quality due to the fact that the position of the blade was parallel to the cutting plane.

Other systems provide manual movement, with the problems already mentioned and with a greater blade oscillation speed provided by a turbine system powered by pressurized nitrogen.

The object of the present invention is precisely to devise a Microkeratotome which overcomes the above-mentioned problems and incorporates qualities which markedly improve both the cutting quality and the control, handling, practicality and performance at the disposal of the surgeon.

BRIEF DESCRIPTION OF THE DRAWINGS

To complement the description that is being given and in order to promote a better understanding of the characteristics of the invention, in accordance with a preferred practical embodiment of the same, and as an integral part of the said description, a set of drawings accompany it in which, in an illustrative and non-restrictive way, the following are represented.

DETAILED DESCRIPTION OF THE PRESENTLY PREFERRED EMBODIMENTS

The Microkeratotome of the invention is conceived to resolve all the problems described hereinbefore, and it is based on the type of apparatus which executes cutting of the corneal lamella, followed by operation of laser equipment on the uncovered area, by means of an automatic linear movement both in the forward and return paths.

The Microkeratotome is made up from a general supporting body on which a chassis is duly placed on which two motors are installed, one of which is connected to a cogwheel having an axle with an eccentric pin, which provides the corresponding cutting blade with oscillation at the desired speed; and another motor, situated in the lower part, intended to drive in a controlled way the movement of the head which houses the blade, through the corresponding suction ring, also at the speed and distance selected, and also driving its return at the desired moment. That is, one motor provides the oscillatory movement, while the other provides the linear movement.

One of the sides of the general supporting body may be opened, having a cover conveniently attached to the said body in such a way that by disassembling it the interior or chassis is exposed with the two motors that make up the transmission system to the corresponding head, all this in such a way that when the side cover is detached and the complete chassis extracted with the motors and transmission mechanisms, the rest may be immersed in sterilizing fluid, thus simplifying and ensuring sterilization of the parts of the Microkeratotome which have been exposed to contact both with the surgeon and the patient. The sterilization systems used by other types of apparatus limit their operation upon the cutting head, which after being detached from the electronic components is immersed in the fluid at a high temperature.

The general body has an upper orifice for passing a single cable for the unified supply of power to the motors and to a sensor, the arrangement of this single cable providing greater manageability at the same time as it takes weight away from the Microkeratotome. Likewise, the body has another orifice in correspondence with the lower front part, which allows it to be connected with the head through an eccentric axle which passes through this orifice and has a retractable eccentric pin which will provide the rocking or oscillatory movement of the cutting blade.

The said head incorporates a transparent plate in its frontal part which in addition to allowing the surgeon to view the cutting area, flattens the cornea and delimits the cutting thickness according to the separation of its rear edge from the edge of the blade, with the peculiarity that the rear part of this head maintains pressure upon the eye when the cut has been made. The shape of the head allows optimal visual tracking, both of the centering upon the cornea of the suction ring and of the operation as it is carried out.

The Microkeratotome also incorporates the above-mentioned suction ring which immobilizes and communicates vacuum pressure to the eyeball through an orifice, distributing this vacuum uniformly by means of a specially designed peripheral channel in the said suction ring; this channel provides a qualitatively better and more uniform suction, the immobilization of the eyeball being more reliable.

The said suction ring remains duly in place without loosening, because at the same time that the unit is attached to the patient's eye, ocular pressure reaches its maximum before the blade begins to cut.

Moreover, this suction and immobilization ring has a complementary dovetail on its upper side of lateral guides situated under the head for assembly and guided sliding between both components.

It also includes an electronic control unit with transmission means which activate the movement and its direction as well as the speed selection of movement and blade action, having several predefined programmes, according t o the keratotomy appropriate for the patient, which combine a determinate blade oscillation speed with the cutting unit's movement speed, and its path and stopping point.

It should be emphasized that once the cut has been finished, having reached the predefined stop, the Microkeratotome allows a new distance or cutting and stopping path to be selected or predefined using the pedal which activates that option, raising and stepping upon it for an additional path of the number of tenths of a millimetre the surgeoen deems appropriate, without altering the quality of the cut with respect to possible imperfections or steps due to the transition from stopping to a fresh start. In this way it is possible in turn to achieve planings of large diameter, if required at the last moment.

The basis of what was stated above lies in the fact that the predefinition of the first cutting stop achieves the corneal hinge or flap, that is, a kind of lentil which is not dissected completely from the cornea and retains at one side what acts subsequently as a kind of hinge to be folded back, leaving a free space for the operation of the myopia-correcting laser, in such a way that this corneal hinge or flap will have a size that could be insufficient once the cut has already been made. For this reason it is considered important to incorporate the possibility of establishing a fresh cutting path that may be selected in tenths of a millimetre, according to the surgeon's judgement, which constitutes a significant advantage as the size of the hinge in question will be provided with suitable dimensions.

It should also be emphasized that the Microkeratotome is to incorporate an auxiliary power supply system in case of electrical failure, which is activated when there is the slightest problem in the connection to the electricity mains, thus providing the operation with stability and reliability; and it also has a Reset system which restores the electrical system to normal conditions in the event that any malfunction in the vacuum system is detected, so that any type of anomaly carries with it the activation of an alarm with visual and acoustic indication, which disables the action of the motors, halting the operation in progress on the cornea.

Moreover, the movement of advance is united with that of cutting, so that the one is not possible without the other in automatic mode, while the return movement is executed without the cutting movement and takes priority over the movement of advance, in the event that the two commands are given simultaneously. A numerical viewer will show the values selected for carrying out the operation, indicating the type of ring used, the cutting speed of the blade in oscillations (revolutions) per minute, the speed of advance in millimetres per second and the linear movement according to keratometry, these values being selected from among several options previously memorized for each of the four foregoing parameters by means of a touch screen. Vacuum pressure is indicated on a digital viewer, allowing selection of the interval of working pressures which will not activate the alarm due to malfunction of the vacuum system.

From the said touch screen and operating only the cutting motor, the manual operation option (manual movement and mechanical stopping point) may be selected.

Consequently, the said Microkeratotome constitutes an apparatus comprising a compact unit which can be used with only one hand, in such a way that the head and ring, the on e previously installed in the other, are applied directly upon the eyeball, being fixed in place by the suction provided through the said ring.

It should also be emphasized that the said apparatus may incorporate a system of quick attachment of the head to the general body, consisting of the body being attached to the cutting head by introducing it into channels on the rear part of the latter, and guiding it with a 90° rotary movement into housings on the he ad itself, fixing the latter in its final position.

In addition to the alarm system mentioned above, which halts both the cutting movement and the path when a vacuum failure is detected, there is the possibility that once the vacuum is restored, according to the judgement of the surgeon, the operation may continue or be halted, and the cutting unit brought back and dismounted.

Turning now to the figures, the Microkeratotome of the invention consists of a general body (1) as a means of support of all the components, which has one of its sides in the form of a detachable cover (2), which is conveniently fixed in place by a screw passing through the orifices (3) of this cover (2) and (4) of the body (1), and in the cover (2) there are also studs (5) by means of which the cover (2) is positioned and centered upon the corresponding side of the body (1).

Figure 2:
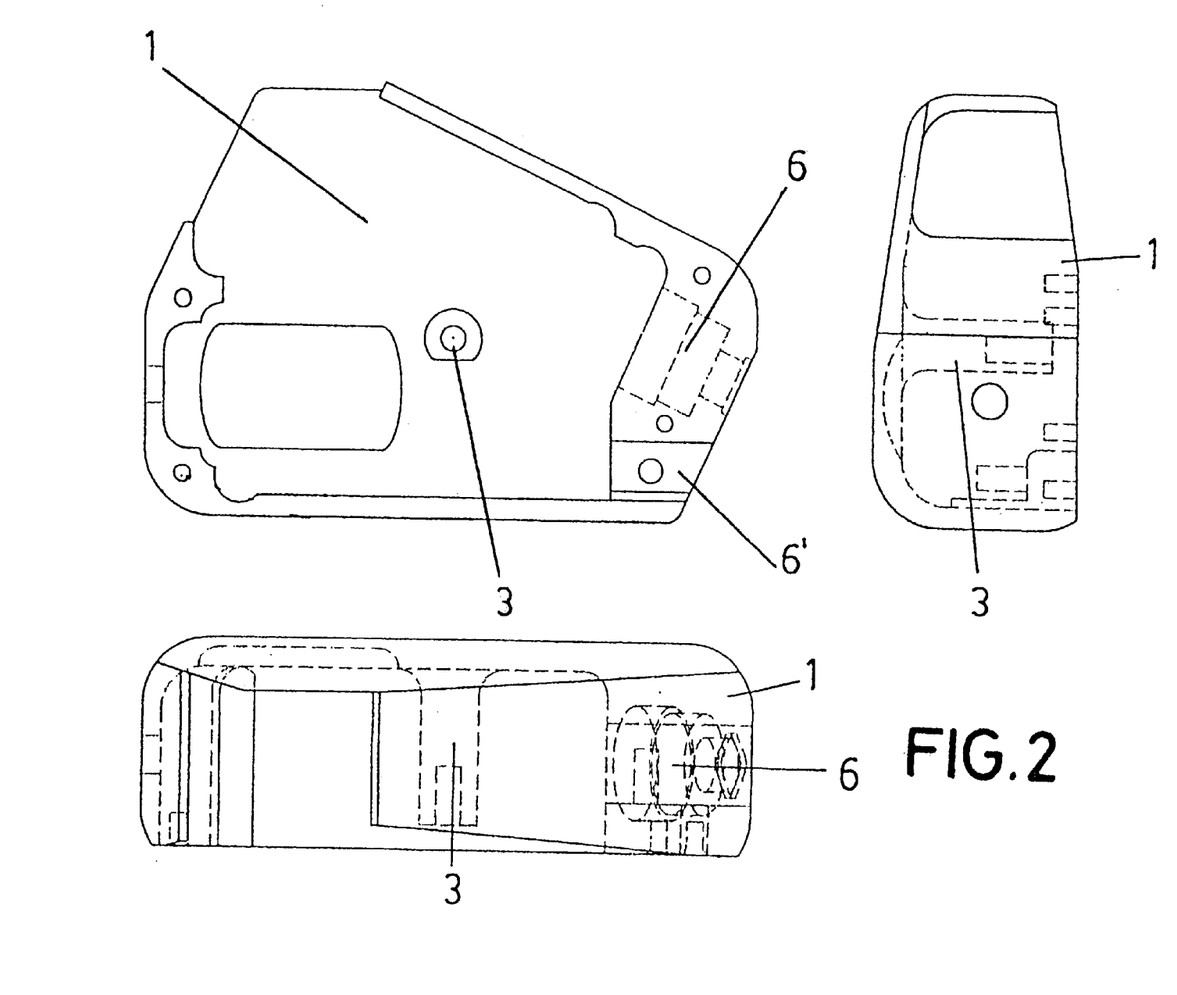
FIG. 2. Shows the views corresponding to a side elevation, a plan view and a profile, of the general body of the Microkeratotome represented in the foregoing figure.
Figure 3:
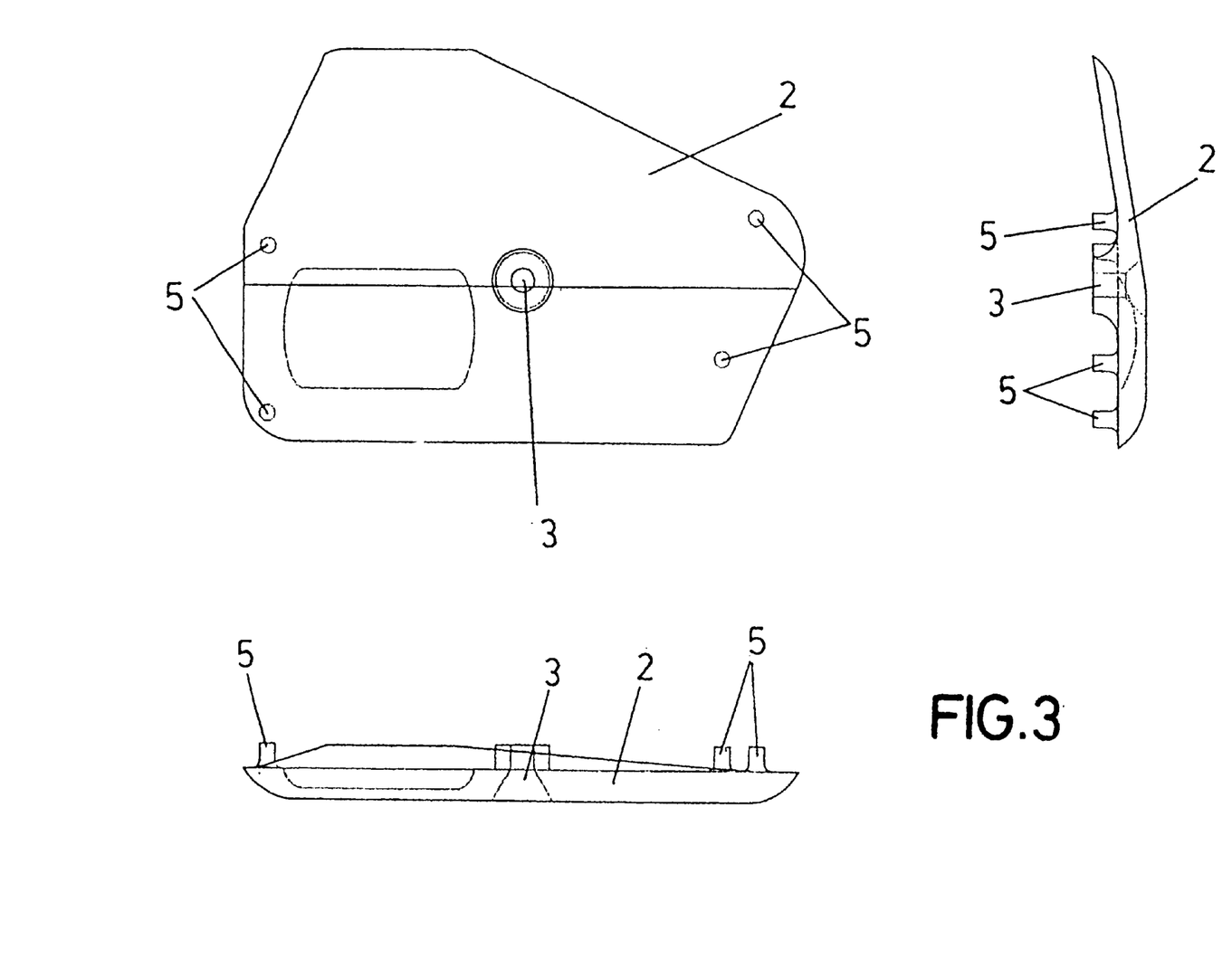
FIG. 3. Shows a side view, another in elevation and yet another in profile of the cover that closes the side of the body represented in the foregoing figure.

The said body (1), as represented in FIG. 2, in addition to the orifice (3) opposite to the corresponding orifice of the cover (2) with the latter's attachment and the housings of the said body (1) for the studs (5) of the cover (2), also includes an orifice (6) having different stepped sections for positioning the elements which guide an eccentric axle (7) whose characteristics and functions will be explained below.

Figures 4, 5:
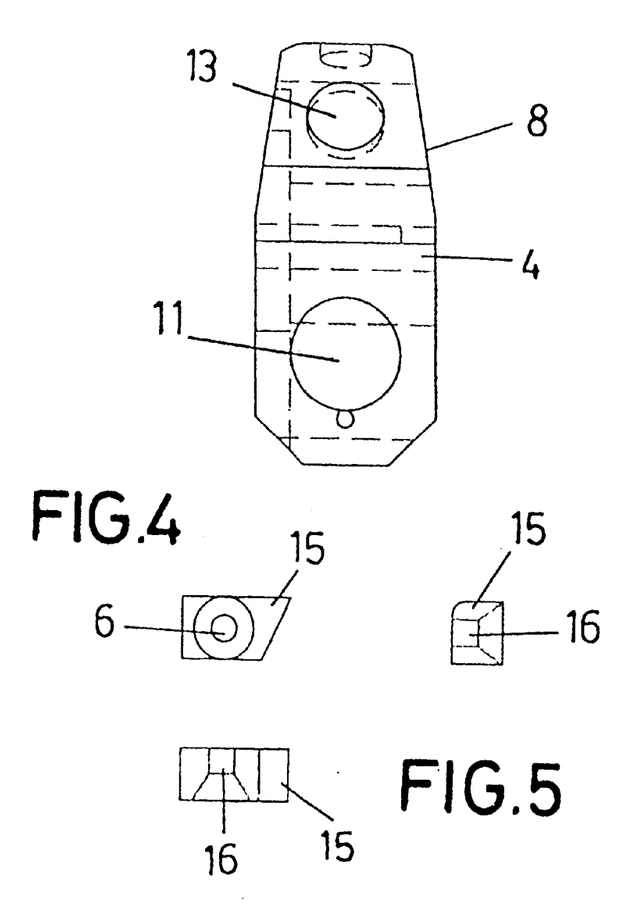
FIG. 4. Shows the views corresponding to a side elevation with a plan view and profile of the extractible chassis in which the motors are mounted which correspond to the mechanical transmission of the Microkeratotome.
FIG. 5. Also shows the three views corresponding to a part acting as a check or stopping point for the anchoring element of the suction ring.

The body (1) has a housing in which a chassis (8) is situated with a special configuration, and in which there is a seating (9) for the mounting and positioning of a motor (10) whose function is to impart the oscillatory movement to the cutting mechanism, also including an orifice (11) for mounting the motor (12) which provides the linear advance movement. It also has in its upper rear part another orifice (13) where the rubber cable holder (14) is situated which channels the electrical power supply to the said motors (10) and (12) and to a sensor whose arrangement and mounting will be explained below. There is also another orifice (4') which is opposite to the orifices (3) of the body (1) and the side cover (2) for fixing the said chassis (8) in place.

After removing the cover (2) it is possible to extract the chassis (8) with the motors (10) and (12), and the other transmission elements associated with the same, so as to be able to carry out sterilization of the unit.

Returning to the body (1), in addition to the above-mentioned orifice (6), it includes another lower one (6') for mounting a check (15) with an orifice (16) for fixing the same in place; the function of this check (15) will be explained below.

Figure 8:
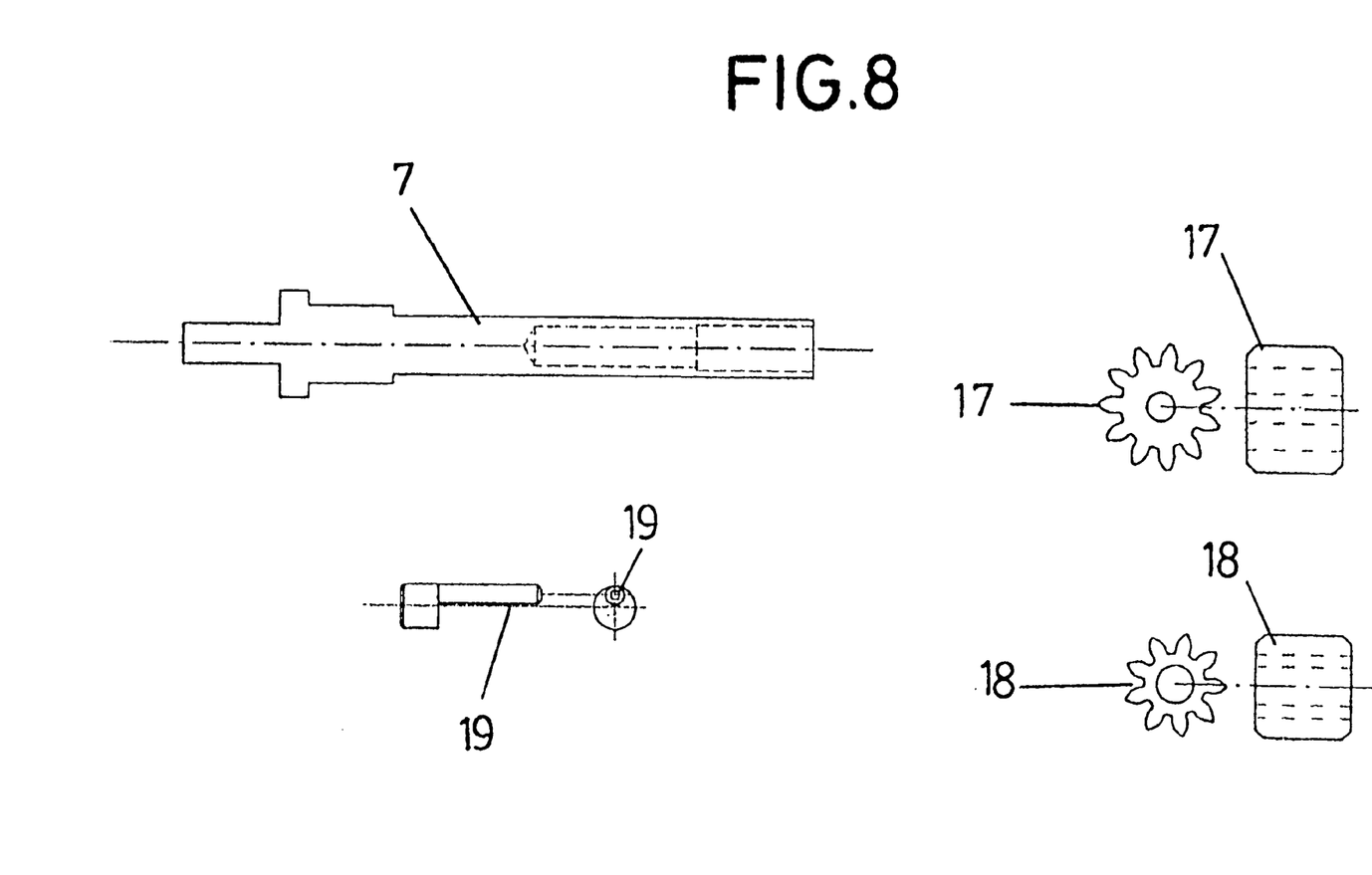
FIG. 8. Shows a side elevation of the eccentric axle, and also the cogwheels and the eccentric pin which are mounted upon the orifice of the lower front part of the Microkeratotome's general body; by means of the said axle the head is connected to the corresponding oscillation motor.

The motors (10) and (12) make up the mechanical transmission system, in such a way that a cogwheel (17) is mounted on the motor (10), which engages with a second wheel (18), the latter being fixed on one of the ends of the eccentric axle (7) which passes through the orifice (6) of the body (1), all of which has the purpose of imparting the oscillatory movement to the corresponding cutting blade (20) on the head (21), with the peculiarity that at the other end of this eccentric axle (7) there is a spring and a retractable pin (19).

Figure 1:
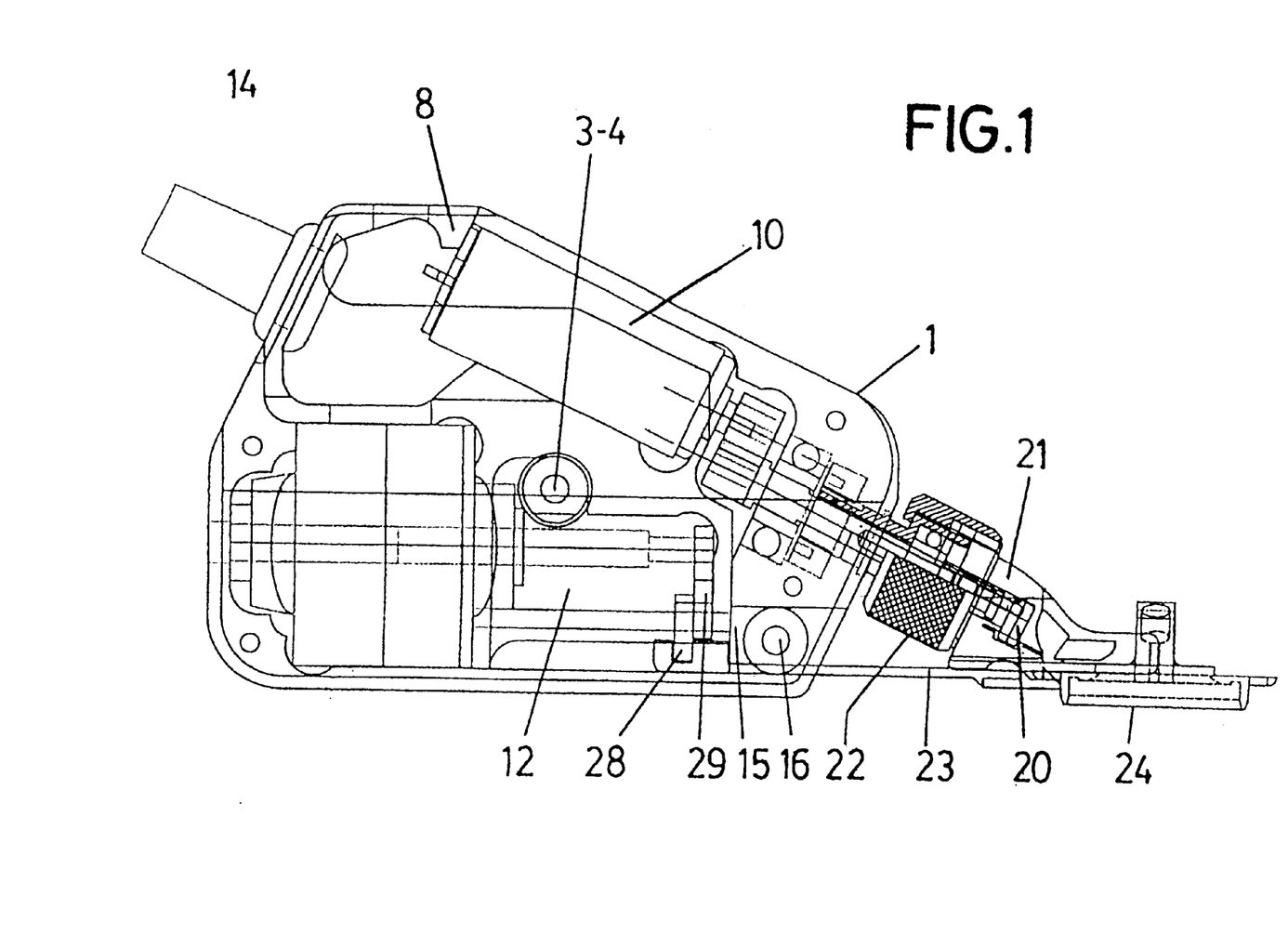
FIG. 1. Shows a representation in diagrammatic side elevation of the Microkeratotome realized in accordance with the object of the invention.

The head (21) is fixed in place by a rapid anchoring device (22) mounted between the eccentric axle (7) and the head itself (21), as represented in FIG. 1.

Figure 6:
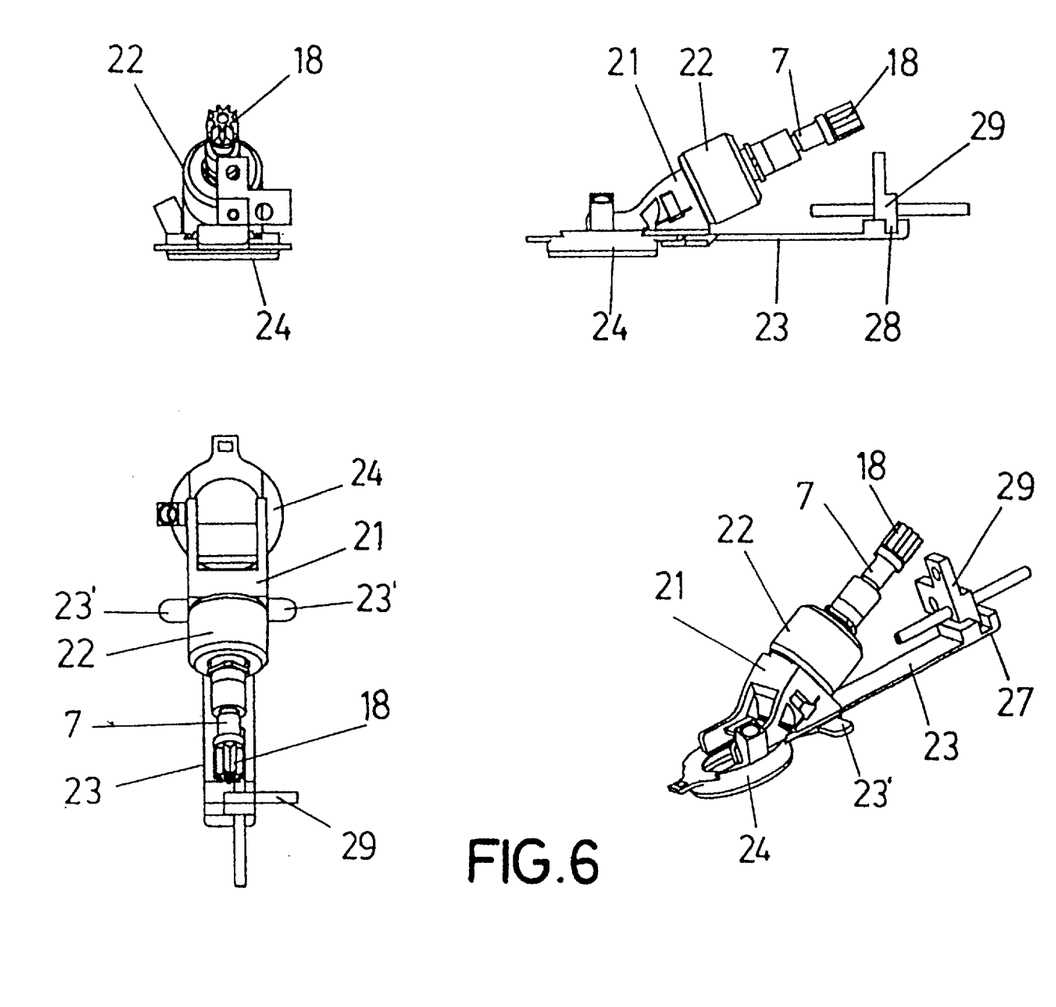
FIG. 6. Shows different views of the unit corresponding to the cutting and advance transmissions which form part of the Microkeratotome of the invention.
Figure 7:
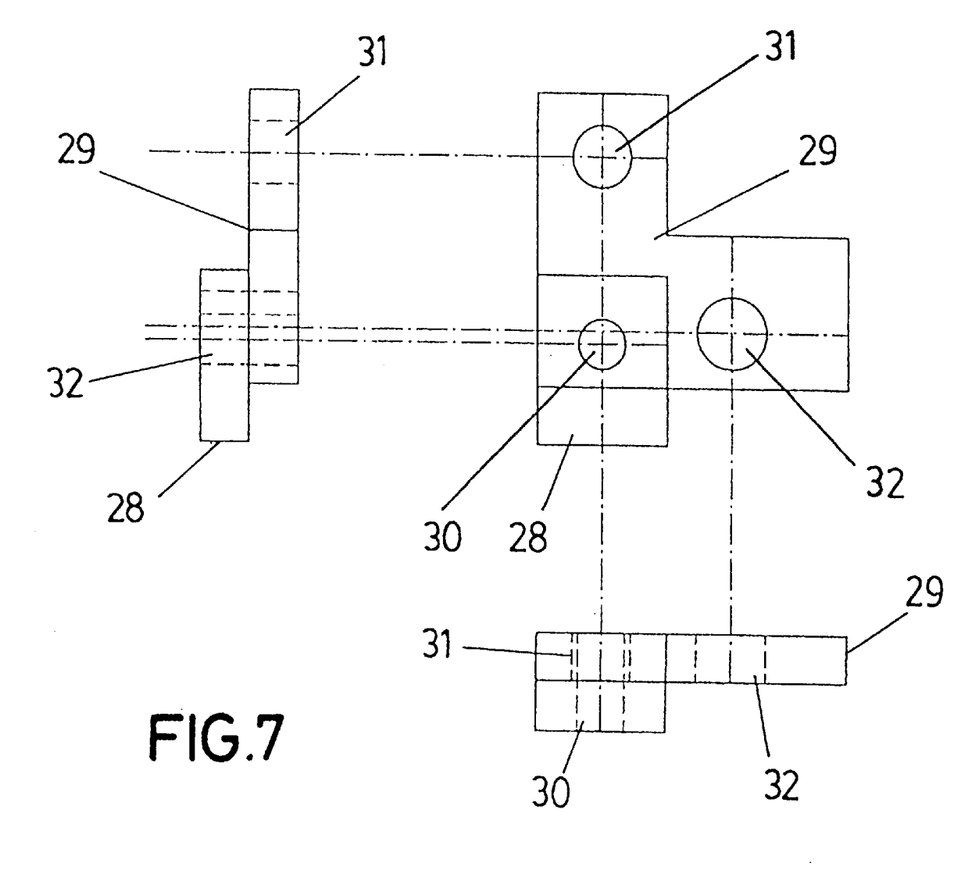
FIG. 7. Also shows elevation, side and profile views of the part which constitutes the guide of the advance system.

In FIG. 6 one may observe the said transmission system made up of the motor block which determines the head (21) with the operating elements of the same and the block which forms an anchoring and sliding part (23) for the suction ring (24), in such a way that this anchoring part (23), which is sliding and flexible, has a fastening claw xx (25) provided at its front end for attaching it to an aperture (26) in the suction ring itself (24), making linear movement of the said ring (24) possible, driven from a slot (27) provided for this purpose in the opposite end of this sliding anchoring part (23). In this slot (27) a flange or projection (28) is introduced belonging to a guiding part (29), which has a traversing orifice (30) through which a metallic bar slides which transmits the advance and return movement from the linear motor (12), whose axle is situated upon the orifice (31) of this guiding part (29), which also has an orifice (32) for mounting the above-mentioned electromagnetic sensor which will move together with the guide itself (29), activating when the latter reaches the end of its path, which corresponds to the initial or rest position.

Figure 9:
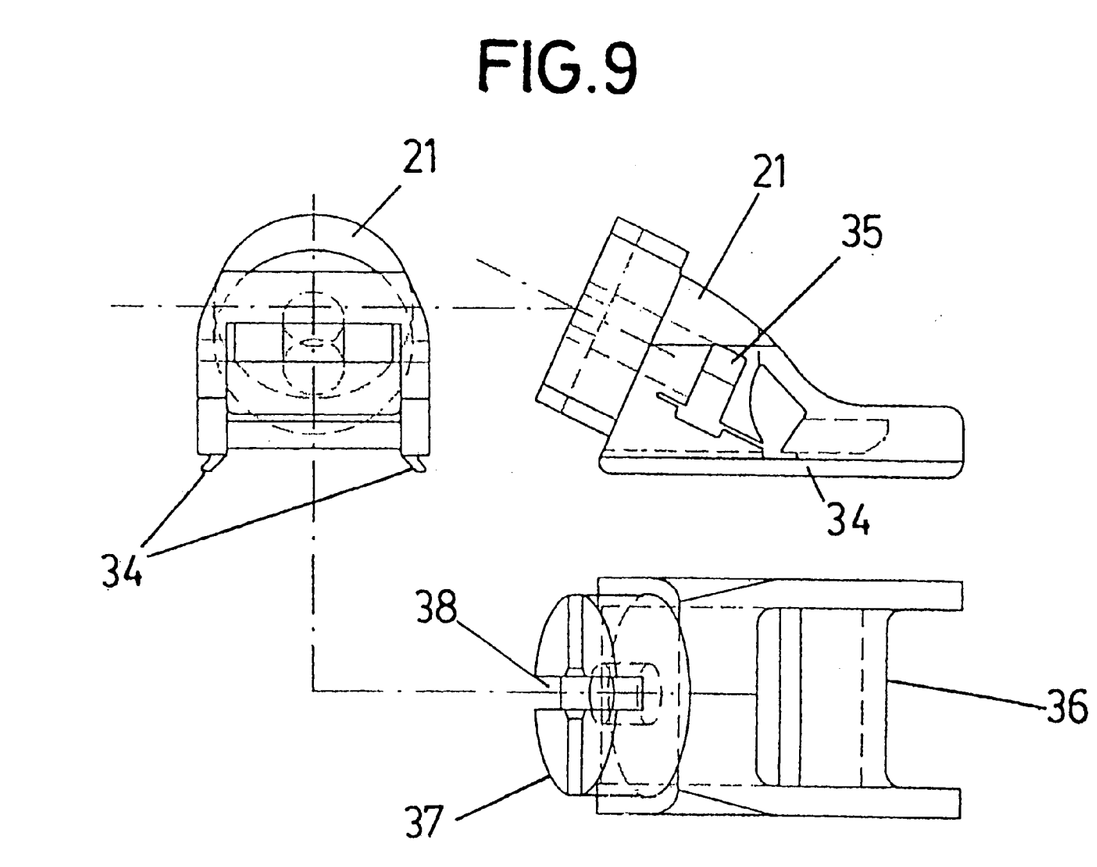
FIG. 9. Also shows three views of the head which forms part of the Microkeratotome of the invention.

The check or stopping point (15) provided in the orifice (6') of the body (1) allows the said sliding anchoring part (23) to remain upon the said body; and by means of the said sliding anchoring part (23) the suction ring (24) moves, which has a dovetail projection (33) for the sliding mounting of the head (21), as the latter has complementary and internal legs (34), as may clearly be observed in FIG. 9, all of which in such a way that when a blade conveniently installed in an oscillating blade-holder slides along a slot (35) in the head itself (21), it produces in combination with the advancing movement of the part (23), which is activated by the linear motor (12), the cutting of the corneal lamella whose thickness is determined by the position of a transparent flattening plate (36) provided in the head itself (21), which in turn has in its upper rear part a circular threaded body (37), which in combination with slots (38) allows correct fixing of the head itself (21) to the body (1), by means of the nut (22).

Figure 11:
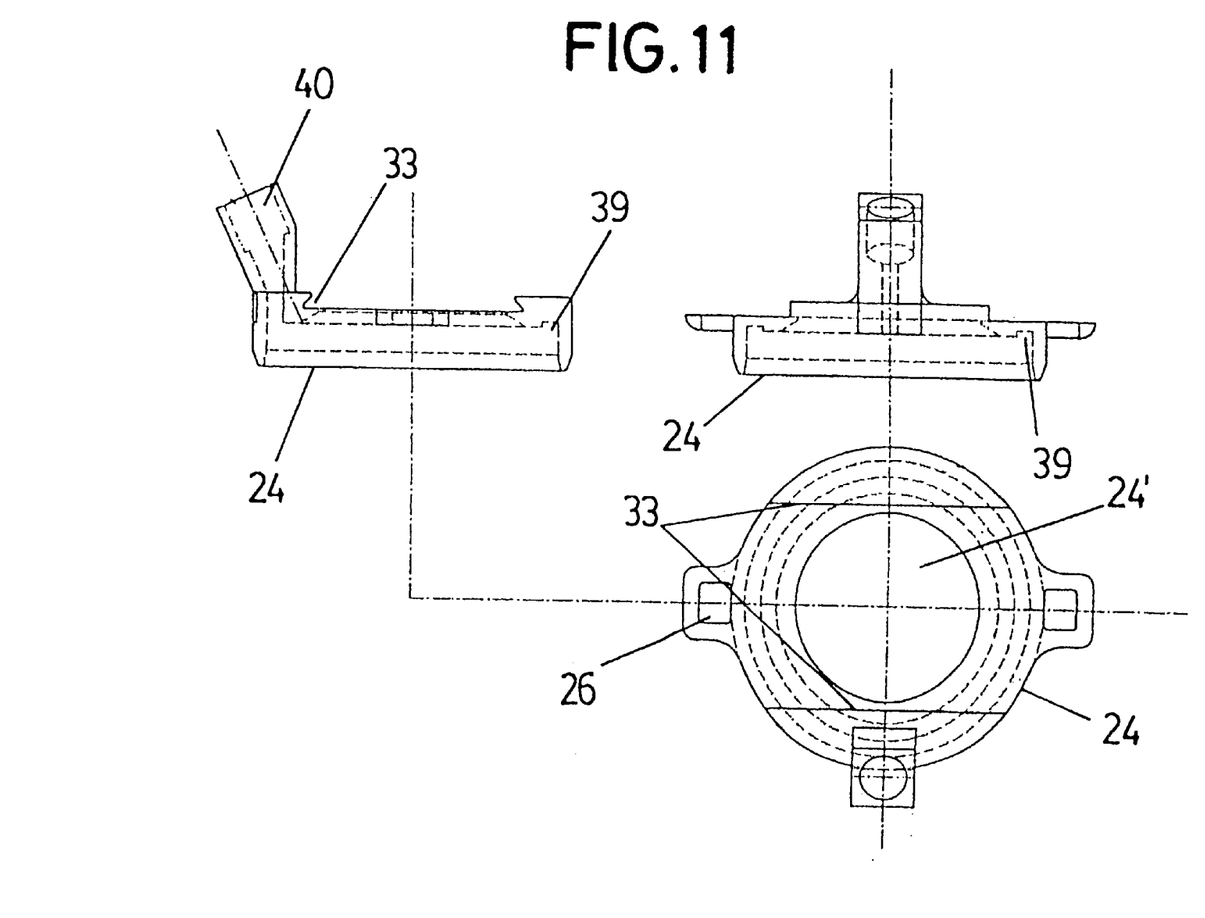
FIG. 11. Shows three views, corresponding to an elevation, a profile and a plan view, of the suction ring.

The suction ring (24) is provided to immobilize the eyeball which projects through the orifice (24') concentrically positioned in the said ring (24), the suction and therefore the immobilization of the eyeball being effected by means of a depression (vacuum) distributed by means of a peripheral channel (39) provided for this purpose in the ring (24), which is connected to the vacuum pump of a collector (40) into which the corresponding suction tube will be screwed.

Figure 10:
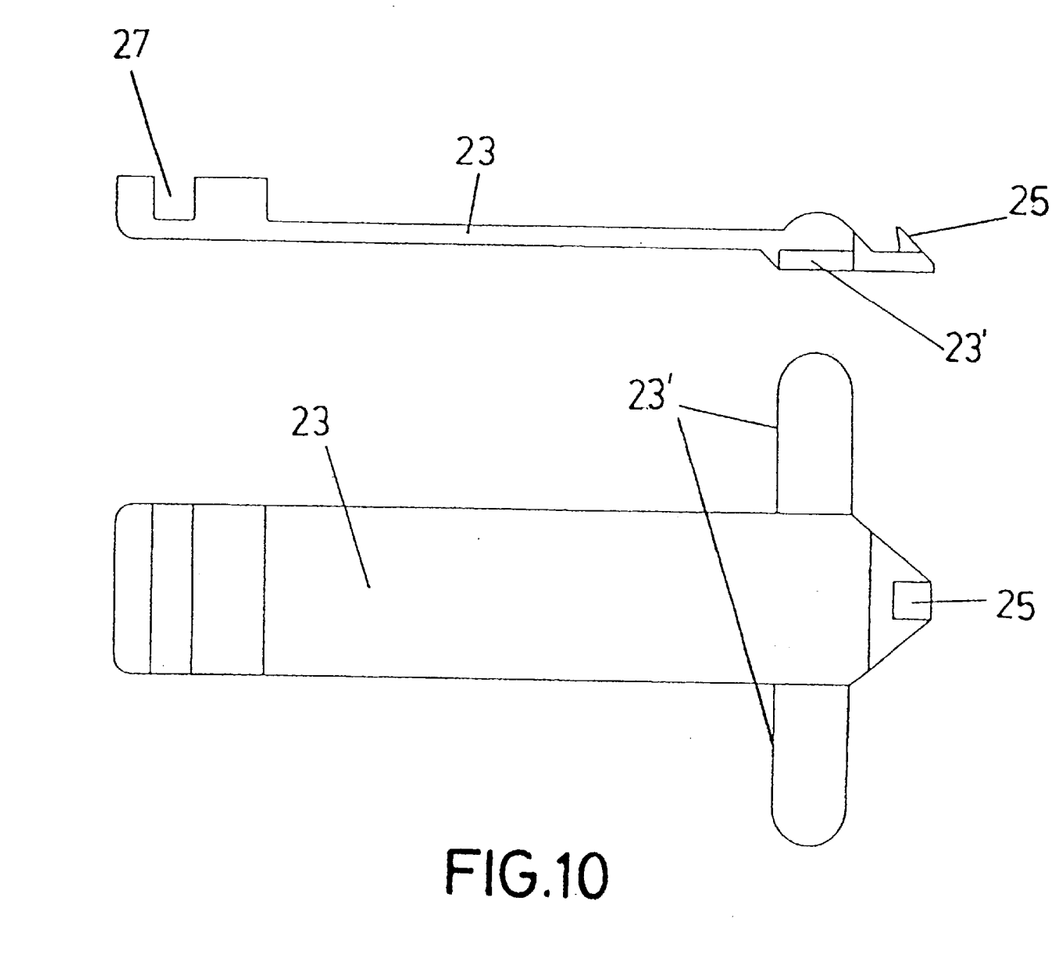
FIG. 10. Shows a side view and another plan view of the anchoring and sliding part of the suction ring.

The sliding anchoring part (23) may be freed by light pressure exerted manually by lateral flanges (23') provided in the front part of the part itself (23).

What is claimed is:

1. A microkeratotome for the dissection of lamellae of corneal tissue, said microkeratotome comprising:
   a suction ring configured for immobilizing an eyeball;
   a sliding and anchoring part positioned adjacent to said suction ring;
   a head comprising a cutting unit, said cutting unit comprising a cutting blade, said head positioned adjacent to said sliding and anchoring part;
   a body connected to said head through an axle, said body comprising:
      a mechanical transmission system comprising:
         an oscillation motor for imparting oscillatory movement to said cutting blade; and
         a linear motor for imparting linear movement to said sliding and anchoring part; and
      a side cover detachably connected to said body, such that detachment of said side cover enables removal of said mechanical transmission system.

2. The microkeratotome of claim 1, wherein said body further comprises an extractible chassis, said chassis comprising means for mounting and positioning said oscillation motor and said linear motor, wherein said chassis, together with said mechanical transmission system, can be removed from said body.

3. The microkeratotome of claim 1, wherein said head further comprises a transparent plate positioned towards a frontal part of said head, wherein said plate is configured for flattening a cornea, is shaped so as to allow visual tracking of an operation, and comprises a rear edge, such that the separation between said rear edge and an edge of said cutting blade delimits a cutting thickness of said cornea.

4. The microkeratotome of claim 1, further comprising an electronic control unit having a plurality of programs, wherein said programs control oscillation speeds of said cutting blade, and paths advancement speeds, and stopping points of said cutting unit.

5. The microkeratotome of claim 4, wherein one or more of said programs is selected according to the needs of a patient's keratometry.

6. The microkeratotome of claim 1, wherein said suction ring comprises a peripheral channel by means of which vacuum pressure can be distributed to said eyeball uniformly and perimetrically.

7. The microkeratotome of claim 6, wherein said suction ring is held in place with respect to said eyeball by means of an increase in ocular pressure.

8. The microkeratotome of claim 6, further comprising an electronic control unit having a plurality of programs, wherein said programs control oscillation speed of said cutting blade, and the path, advancement speed, and stopping point of said cutting unit.

9. The microkeratotome of claim 8, further comprising a reset system which, in the event of a malfunction in said vacuum pressure, activates an alarm system thereby immobilizing said cutting unit, provides visual and acoustic indications of said malfunction, and disables said oscillation motor and said linear motor.

10. The microkeratotome of claim 9, wherein said reset system is configured for resetting said electronic control unit, thereby enabling resumption of an operation once said vacuum pressure has been restored.

11. The microkeratotome of claim 1, further comprising an electromechanical sensor which resets an impulse counter, said impulse counter controlling linear movement of said head when said head is in an initial position, allowing control of a closed loop.

* * * * *